(12) United States Patent
Brichant et al.

(10) Patent No.: US 10,279,282 B2
(45) Date of Patent: May 7, 2019

(54) PROCESS FOR PURIFICATION OF AN ORGANIC ACID INCLUDING AN ELECTRODIALYSIS TREATMENT STEP

(71) Applicant: NOVASEP PROCESS SAS, Pompey (FR)

(72) Inventors: Damien Brichant, Sarzeau (FR); Benjamin Boissier, Lyons (FR); Patrick Dupuy, Villeurbanne (FR)

(73) Assignee: Novasep Process SAS, Pompey (FR)

( * ) Notice: Subject to any disclaimer, the term of this patent is extended or adjusted under 35 U.S.C. 154(b) by 0 days.

(21) Appl. No.: 15/557,568

(22) PCT Filed: Mar. 12, 2015

(86) PCT No.: PCT/EP2015/055229
§ 371 (c)(1),
(2) Date: Sep. 12, 2017

(87) PCT Pub. No.: WO2016/141997
PCT Pub. Date: Sep. 15, 2016

(65) Prior Publication Data
US 2018/0093199 A1    Apr. 5, 2018

(51) Int. Cl.
*B01D 15/08*    (2006.01)
*B01D 61/42*    (2006.01)
(Continued)

(52) U.S. Cl.
CPC .......... *B01D 15/08* (2013.01); *B01D 61/422* (2013.01); *B01D 61/58* (2013.01); *B01D 65/02* (2013.01);
(Continued)

(58) Field of Classification Search
CPC .......... C07C 51/02; C07C 51/42; C07C 51/47; C07C 51/487; C07C 59/08; C07C 59/265; B01D 15/08; B01D 61/422
See application file for complete search history.

(56) References Cited

U.S. PATENT DOCUMENTS

| 5,245,078 | A | * | 9/1993 | Maeda | .................... | C07C 51/47 |
| | | | | | | 562/580 |
| 5,641,406 | A | * | 6/1997 | Sarhaddar | ............... | C07C 51/47 |
| | | | | | | 210/198.2 |

(Continued)

FOREIGN PATENT DOCUMENTS

| CN | 101607887 | A | * | 12/2009 | ............. | C07C 51/47 |
| CN | 102220388 | A | * | 10/2011 | ............. | C07C 51/42 |

(Continued)

OTHER PUBLICATIONS

CN 101607887 (A), Wei Cong, Method for cleanly producing lactic acid by fermentation method, English Translation, pp. 1-46 (Year: 2009).*

(Continued)

*Primary Examiner* — Yate' K Cutliff
(74) *Attorney, Agent, or Firm* — Hamilton, Brook, Smith & Reynolds, P.C.

(57) ABSTRACT

It is an object of the invention to provide a process for producing an organic acid, comprising: providing an incoming stream containing an organic acid and impurities; subjecting said incoming stream to a step of chromatographic separation, using a solution of mineral acid as an eluent, so as to collect an extract and a raffinate, the organic acid being recovered in the extract; and subjecting the raffinate to an electrodialysis step, so as to collect a diluate and a concentrate, the mineral acid being concentrated in the concentrate. The invention also provides an installation for implementing this process.

11 Claims, 2 Drawing Sheets

(51) Int. Cl.
  B01D 61/58   (2006.01)
  C07C 51/47   (2006.01)
  C07C 51/48   (2006.01)
  C07C 51/44   (2006.01)
  B01D 65/02   (2006.01)
  C07C 59/265  (2006.01)
  C07C 51/42   (2006.01)
  B01D 15/18   (2006.01)
  B01D 61/02   (2006.01)

(52) U.S. Cl.
  CPC .............. *C07C 51/44* (2013.01); *C07C 51/47* (2013.01); *C07C 51/48* (2013.01); *C07C 59/265* (2013.01); *B01D 15/1821* (2013.01); *B01D 61/025* (2013.01); *B01D 2311/04* (2013.01); *B01D 2311/06* (2013.01); *B01D 2311/08* (2013.01); *B01D 2311/25* (2013.01); *B01D 2311/2623* (2013.01); *B01D 2311/2626* (2013.01); *B01D 2311/2673* (2013.01); *B01D 2321/04* (2013.01); *C07C 51/42* (2013.01)

(56) References Cited

U.S. PATENT DOCUMENTS

| | | | | |
|---|---|---|---|---|
| 6,280,985 | B1* | 8/2001 | Caboche | B01D 61/445 435/136 |
| 2013/0245320 | A1* | 9/2013 | Yoshida | C07C 51/42 562/580 |
| 2014/0371486 | A1* | 12/2014 | Schulze | C07C 51/47 562/580 |

FOREIGN PATENT DOCUMENTS

| | | |
|---|---|---|
| CN | 102220388 A | 10/2011 |
| EP | 1 078 911 A2 | 2/2001 |
| EP | 1 094 054 A1 | 4/2001 |
| JP | 8-325191 A | 12/1996 |

OTHER PUBLICATIONS

CN 1012220388 (A), Wei Cong, Method for clean production of lactic acid by calcium salt process, English Translation . . . 1-25 (Year: 2011).*

Egggeman, T., et al., Recovery of Organic ACids from Fermentation Borths, 2005, Applied Biochemistry and Biotechnology, vol. 121-124, pp. 605-618 (Year: 2005).*

Pinacci, P., et al., Recovey of citric acid from fermentation broths by electrodialysis with bipolar membranes, 2002, Desalination, No. 148, pp. 177-179 (Year: 2002).*

International Search Report, International Application No. PCT/EP2015/055229 Titled: "Process for Purification of an Organic Acid Including an Electrodialysis Treatment Step," dated Sep. 11, 2015, 4 pages.

Written Opinion of the International Searching Authority, International Application No. PCT/EP2015/055229 Titled: "Process for Purification of an Organic Acid Including an Electrodialysis Treatment Step," dated Sep. 11, 2015, 6 pages.

* cited by examiner

PROCESS FOR PURIFICATION OF AN ORGANIC ACID INCLUDING AN ELECTRODIALYSIS TREATMENT STEP

This application is the U.S. National Stage of International Application No. PCT/EP2015/055229, filed Mar. 12, 2015, which designates the U.S., published in English. The entire teachings of the above application are incorporated herein by reference.

TECHNICAL FIELD

The present invention relates to a process for purifying organic acids, such as citric acid, comprising a step of chromatographic separation and electrodialysis treatment step, as well as to an installation for implementing this process.

TECHNICAL BACKGROUND

The fermentative production of organic acids results in aqueous culture broths containing dissolved organic acids, microorganisms and impurities essentially consisting of residues of substrates and cell metabolism of said microorganisms.

A traditional method for purifying an organic acid from a fermentation broth consists in forming an insoluble calcium salt of organic acid, by contacting the broth with lime, and then recovering said salt by filtration. The salt of organic acid is then treated by adding sulfuric acid. After a further filtration step, an aqueous solution of organic acid is collected on the one hand, and insoluble gypsum (calcium sulfate) is collected as waste on the on the other hand.

This technique requires large amounts hot water and sulfuric acid, and it leads to the production of large amounts of gypsum waste without market value.

Chromatography-based processes have also been proposed as alternative solutions, offering reduced operation costs and requiring less effluent treatment. Document FR 2900654 describes such a chromatography-based process for the purification of organic acids. In the chromatographic separation step (also called acid retardation step) of this kind of process, diluted acidic water is used as the eluent. As a result, a raffinate waste stream is produced, which contains mineral acid at a relatively large concentration. Such an acidic effluent raises environmental concerns and is not easy to efficiently treat.

Document FR 3005428 describes a process of recycling a regeneration effluent in an ion exchange process, using electrodialysis. The effluent which is subjected to the electrodialysis treatment contains a high concentration of chloride ions.

There is therefore still a need for efficiently treating and valorizing effluent streams in processes for the production of organic acids.

SUMMARY OF THE INVENTION

It is a first object of the invention to provide a process for producing an organic acid, comprising:
providing an incoming stream containing an organic acid and impurities;
subjecting said incoming stream to a step of chromatographic separation, using a solution of mineral acid as an eluent, so as to collect an extract and a raffinate, the organic acid being recovered in the extract; and
subjecting the raffinate to an electrodialysis step, so as to collect a diluate and a concentrate, the mineral acid being concentrated in the concentrate.

According to one embodiment, the solution of mineral acid is selected from a solution of sulfuric acid, phosphoric acid, nitric acid, hydrochloric acid and combinations thereof.

According to one embodiment, the organic acid comprises citric acid.

According to one embodiment, the eluent contains less than 20 g/L, preferably less than 10 g/L, more preferably less than 5 g/L, more preferably less than 2 g/L and most preferably less than 1 g/L mineral acid.

According to one embodiment, the diluate is subjected to a concentration step, preferably by evaporation or reverse osmosis, so as to collect a diluted fraction on the one hand and a concentrated fraction on the other hand.

According to one embodiment:
at least part of the concentrate, and preferably all of the concentrate, is recycled with the incoming stream; and/or
at least part of the diluted fraction, and preferably all of the diluted fraction, is recycled with the incoming stream.

According to one embodiment:
at least part of the concentrate, and preferably all of the concentrate, is recycled with the eluent in the step of chromatographic separation; and/or
at least part of the diluted fraction, and preferably all of the diluted fraction, is recycled with the eluent in the step of chromatographic separation.

According to one embodiment, providing the incoming stream comprises at least one of the following steps, and preferably all of the following steps:
an upstream fermentation step;
an upstream filtration step;
an upstream ion exchange step; and
an upstream evaporation step.

According to one embodiment:
at least part of the concentrate, and preferably all of the concentrate, is recycled as a feed in the upstream fermentation step; and/or
at least part of the diluted fraction, and preferably all of the diluted fraction, is recycled as a feed in the upstream fermentation step.

According to one embodiment:
at least part of the concentrate, and preferably all of the concentrate, is recycled in the upstream filtration step, notably as a diluent or as a cleaning stream; and/or
at least part of the diluted fraction, and preferably all of the diluted fraction, is recycled in the upstream filtration step, notably as a diluent or as a cleaning stream.

According to one embodiment:
at least part of the concentrate, and preferably all of the concentrate, is recycled in the upstream ion exchange step, notably as a regeneration stream; and/or
at least part of the diluted fraction, and preferably all of the diluted fraction, is recycled in the upstream ion exchange step, notably as a regeneration stream.

According to one embodiment:
at least part of the concentrate, and preferably all of the concentrate, is recycled in the upstream evaporation step, notably as a cleaning stream; and/or
at least part of the diluted fraction, and preferably all of the diluted fraction, is recycled in the upstream evaporation step, notably as a cleaning stream.

According to one embodiment, the extract is subjected to at least one of the following steps, and preferably all of the following steps:
- a downstream adsorption step, or a downstream ion exchange step, or a downstream treatment step on activated carbon;
- a downstream evaporation step; and
- a downstream crystallization step.

According to one embodiment:
- at least part of the concentrate, and preferably all of the concentrate, is recycled in the downstream ion exchange adsorption step or ion exchange step or treatment step on activated carbon, notably as a regeneration stream; and/or
- at least part of the diluted fraction, and preferably all of the diluted fraction, is recycled in the downstream ion exchange adsorption step or ion exchange step or treatment step on activated carbon, notably as a regeneration stream.

According to one embodiment:
- at least part of the concentrate, and preferably all of the concentrate, is recycled in the downstream evaporation step, notably as a cleaning stream; and/or
- at least part of the diluted fraction, and preferably all of the diluted fraction, is recycled in the downstream evaporation step, notably as a cleaning stream.

According to one embodiment:
- at least part of the concentrate, and preferably all of the concentrate, is recycled in another process, other than the process for producing an organic acid; and/or
- at least part of the diluted fraction, and preferably all of the diluted fraction, is recycled in another process, other than the process for producing an organic acid.

It is another object of the invention to provide an installation for producing an organic acid, comprising:
- a chromatographic separation unit;
- an electrodialysis unit;
- an incoming stream line and an eluent line connected to inlets of the chromatographic separation unit, wherein the eluent in the eluent line is a solution of mineral acid and the incoming stream in the incoming stream line contains an organic acid;
- an extract line for recovering the organic acid, and a raffinate line, both connected to outlets of the chromatographic separation unit, the raffinate line being connected to an inlet of the electrodialysis unit;
- a diluate line and a concentrate line connected to outlets of the electrodialysis unit.

According to one embodiment, the organic acid comprises citric acid.

According to one embodiment, the solution of mineral acid is selected from solutions of sulfuric acid, phosphoric acid, nitric acid, hydrochloric acid and combinations thereof.

According to one embodiment, the eluent contains less than 20 g/L, preferably less than 10 g/L, more preferably less than 5 g/L, more preferably less than 2 g/L and most preferably less than 1 g/L mineral acid.

According to one embodiment, the installation further comprises:
- a concentration unit, fed by the diluate line, and which is preferably an evaporation unit or a reverse osmosis unit;
- a diluted fraction line and a concentrated fraction line connected to outlets of the concentration unit.

According to one embodiment:
- the concentrate line at least partly and preferably completely feeds a recycle line which is connected to the incoming stream line; and/or
- the diluted fraction line at least partly and preferably completely feeds a recycle line which is connected to the incoming stream line.

According to one embodiment:
- the concentrate line at least partly and preferably completely feeds a recycle line which is connected to the eluent line; and/or
- the diluted fraction line at least partly and preferably completely feeds a recycle line which is connected to the eluent line.

According to one embodiment, the installation further comprises, upstream of the incoming stream line:
- an upstream fermentation unit;
- an upstream filtration unit;
- an upstream ion exchange unit; and
- an upstream evaporation unit.

According to one embodiment:
- the concentrate line at least partly and preferably completely feeds the upstream fermentation unit; and/or
- the diluted fraction line at least partly and preferably completely feeds the upstream fermentation unit.

According to one embodiment:
- the concentrate line at least partly and preferably completely feeds the upstream filtration unit, notably as a line of diluent or of cleaning stream; and/or
- the diluted fraction line at least partly and preferably completely feeds the upstream filtration unit, notably as a line of diluent or of cleaning stream.

According to one embodiment:
- the concentrate line at least partly and preferably completely feeds the upstream ion exchange unit, notably as a line of regeneration stream; and/or
- the diluted fraction line at least partly and preferably completely feeds the upstream ion exchange unit, notably as a line of regeneration stream.

According to one embodiment:
- the concentrate line at least partly and preferably completely feeds the upstream evaporation unit, notably as a line of cleaning stream; and/or
- the diluted fraction line at least partly and preferably completely feeds the upstream evaporation unit, notably as a line of cleaning stream.

According to one embodiment, the installation further comprises, downstream of the extract line:
- a downstream adsorption unit, or downstream ion exchange unit, or downstream activated carbon treatment unit;
- a downstream evaporation unit; and
- a downstream crystallization unit.

According to one embodiment:
- the concentrate line at least partly and preferably completely feeds the downstream adsorption unit, or downstream ion exchange unit, or downstream activated carbon treatment unit, notably as a line of regeneration stream; and/or
- the diluted fraction line at least partly and preferably completely feeds the downstream adsorption unit, or downstream ion exchange unit, or downstream activated carbon treatment unit, notably as a line of regeneration stream.

According to one embodiment:
- the concentrate line at least partly and preferably completely feeds the downstream evaporation unit, notably as a line of cleaning stream; and/or the diluted fraction line at least partly and preferably completely feeds the downstream evaporation unit, notably as a line of cleaning stream.

According to one embodiment:

the concentrate line at least partly and preferably completely feeds another installation, other than the installation for producing an organic acid; and/or the diluted fraction line at least partly and preferably completely feeds another installation, other than the installation for producing an organic acid.

The present invention relies on the use of electrodialysis for treating a mineral acid-containing raffinate from a chromatographic separation step, in a process for producing an organic acid.

This makes it possible to recycle part or all of the raffinate acids in the process itself, or in another process, thus obviating the need to dispose of large amounts of mineral acid.

It has been found that the electrodialysis step of the invention is effective in concentrating salts or acids from the raffinate, although the initial concentration of these salts and acids is significantly lower than in typical streams which are subjected to electrodialysis in other industrial processes.

Without wishing to be bound by any theory, the present inventors believe that this is made possible owing to the particular composition of the raffinate, which has a low viscosity (since it has a relatively low sugar content), and which contains very mobile and highly conductive ions, such as sulfate ions or protons. Therefore, electrodialysis separation is efficient despite low salt and acid concentrations.

The invention makes it possible to reduce the consumption of mineral acid in the process to less than 75%, or less than 50%, or less than 25%, or less than 10%, or less than 5%, or less than 1%, by weight, of the amount of mineral acid required for producing the same amount of organic acid in the same process but without any electrodialysis step and downstream recycling.

Furthermore, since the invention makes it possible to recover a large fraction of the mineral acid used in the eluent, it is possible to increase the concentration of the mineral acid in the eluent, and accordingly increase the efficiency of the step of chromatographic separation. For instance, according to the invention, the concentration of the mineral acid in the eluent can be greater than 5 g/L, or greater than 10 g/L, or greater than 15 g/L, and may e.g. range up to 20 g/L. In the prior art, a typical concentration of mineral acid in the eluent is only 2 g/L.

The invention also makes it possible to make efficient use of other mineral acids than sulfuric acid. Correlatively, it becomes possible to use other stationary phases than an anionic resin in sulfate form, which is most commonly used. In other terms, the invention improves the versatility of the process.

DESCRIPTION OF EMBODIMENTS

The invention will now be described in more detail without limitation in the following description.

Unless indicated otherwise, percentages are indicated by weight.

Figure 1:
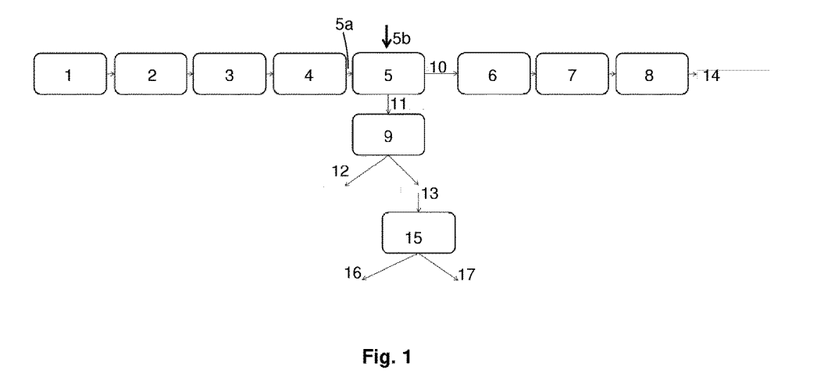
FIG. 1 illustrates one embodiment of the installation of the invention, in a schematic manner.

Making reference to FIG. 1, an installation of the invention comprises at least a chromatographic separation unit 5 coupled with an electrodialysis unit 9. One or more units can be provided upstream or downstream of the chromatographic separation unit 5. These other units are optional. They can thus either be totally absent, or they can be present in another installation, to which the installation of the invention is coupled.

Upstream of the chromatographic separation unit 5, the following units may in particular be provided:

an upstream fermentation unit 1;

an upstream filtration unit 2;

an upstream ion exchange unit 3; and an upstream evaporation unit 4.

Preferably, all these units are provided in this particular order, as illustrated on the drawing. Alternatively, only some of these units can be omitted. For instance, the upstream filtration unit 2 can directly feed the upstream evaporation unit 4 (without any intermediate ion exchange unit); or the upstream ion exchange unit 3 can directly feed the chromatographic separation unit 5 (without intermediate evaporation unit); or the upstream filtration unit 2 can directly feed the chromatographic separation unit 5 (without intermediate ion exchange unit nor evaporation unit).

In the context of the present application, every time a line is said to be connected, or directly connected, to an inlet of a unit, or is said to feed or directly feed a unit, it should be understood that an intermediate buffer tank may optionally be provided, so that the line may optionally feed the unit via the intermediate buffer tank.

The upstream fermentation unit 1, when present, provides a fermentation broth which contains at least one organic acid as well as various impurities.

The organic acid can in particular be citric acid. Other examples include lactic acid, succinic acid or tartaric acid. Mixtures of two or more organic acids can also be used as "the organic acid" in the context of the present invention.

The various units situated downstream of the upstream fermentation unit 1 make it possible to purify the organic acid from the fermentation broth.

The upstream filtration unit 2 can in particular be a microfiltration or an ultrafiltration unit. It may for instance be used to remove solids in suspension from the fermentation broth.

The upstream ion exchange unit 3 is used to perform demineralization or softening. The upstream ion exchange unit 3 may comprise a cationic resin, in order to remove divalent cations such as calcium or magnesium ions and release monovalent ions (such as sodium, potassium or ammonium ions) instead. The upstream ion exchange unit 3 may also comprise an anionic resin in order to remove chloride ions.

The upstream evaporation unit 4 can be used to reduce the volume of the organic acid-containing stream before entry into the chromatographic separation unit 5. The upstream evaporation unit 4 can for instance comprise or can be a falling film evaporator with forced recirculation, a rising evaporator, a flash evaporator, or any other type of evaporator known in the art.

In the chromatographic separation unit 5, a step of chromatographic separation is performed, also called acid retardation. In this step, the organic acid is separated from a number of impurities. Such impurities may in particular include sugars or sugar derivatives and colors.

The chromatographic separation step generally comprises passing an incoming stream, which is an organic acid-containing stream e.g. collected from the upstream evaporation unit 4 or from any other of the above upstream treatment units, onto a bed of a stationary phase. The organic acid is more retained on the stationary phase than the impurities. It is eluted from the stationary phase using an eluent, which is a solution of mineral acid.

The mineral acid is preferably sulfuric acid. Alternatively, phosphoric acid, nitric acid or hydrochloric acid can also be used. Mixtures of two or more mineral acids can also be used as "the mineral acid" in the context of the present invention.

The concentration of mineral acid in the eluent can be up to 20 g/L, preferably up to 10 g/L, preferably up to 5 g/L, preferably up to 2 g/L and most preferably up to 1 g/L.

The stationary phase and the mineral acid are selected in accordance with each other. For instance, an anionic resin, typically in sulfate form, can be used in conjunction with sulfuric acid as the mineral acid. If the mineral acid is different from the ionic form of the resin, a conversion of the resin form will take place over time.

As a result of the chromatographic separation, at least two streams are collected, namely a raffinate and an extract. The organic acid is "recovered" in the extract. This means that the weight ratio of the organic acid relative to the impurities is higher in the extract than in the incoming stream. Conversely, this weight ratio is lower in the raffinate than in the incoming stream.

Accordingly, at least one incoming stream line 5a and one eluent line 5b are connected to inlets of the chromatographic separation unit 5; and at least one extract line 10 and one raffinate line 11 are connected to outlets of the chromatographic separation unit 5.

The chromatographic separation unit 5 can either be a single column chromatography system or a multicolumn chromatography system. Examples of single column chromatography systems include LPLC (low pressure liquid chromatography), HPLC (high performance liquid chromatography) or CYCLOJET™ (also referred to as steady-state recycling) systems. Examples of multicolumn column chromatography systems include SMB (simulated moving bed), iSMB (improved simulated moving bed), AMB (actual moving bed), VARICOL™, MODICON™, POWERFEED™, DCC (dry column chromatography), MCSGP (multicolumn countercurrent solvent gradient purification) or GSSR (gradient with Steady State Recycle) systems.

According to a preferred embodiment, the chromatographic separation unit 5 and the chromatographic separation step are based on an SSMB (sequential simulated moving bed) system, as described in particular in document FR 2900654.

The organic acid-containing extract can be further purified in a number of downstream treatment steps, performed in a number of downstream treatment units. The following units may in particular be provided:

a downstream adsorption unit 6;
a downstream evaporation unit 7; and
a downstream crystallization unit 8.

Preferably, all these units are provided in this particular order, as illustrated on the drawing. Alternatively, some of these units can be omitted. For instance, the extract line 10 from the chromatographic separation unit 5 can directly feed the downstream evaporation unit 7 (i.e. without any intermediate adsorption unit); or it can directly feed the downstream crystallization unit 8 (i.e. without intermediate adsorption unit or evaporation unit); or the downstream adsorption unit 6 can directly feed the crystallization unit 8 (i.e. without any intermediate evaporation unit).

The downstream adsorption unit 6 can be used to perform a polishing step, in particular for substantially removing residual colors which may remain in the extract collected from the chromatographic separation unit 5.

Instead of an adsorption unit, an ion exchange unit or an activated carbon treatment unit can be used.

The downstream evaporation unit 7 can be used to reduce the volume of the organic acid-containing stream before entry into the crystallization unit 8. The downstream evaporation unit 7 can for instance comprise or can be a falling film evaporator with forced recirculation, a rising evaporator, a flash evaporator, or any other type of evaporator known in the art.

The crystallization unit 8 performs crystallization of the organic acid and makes it possible to collect crystals of the organic acid, in a product line 14.

A remaining solution is also collected; it is known as a mother liquor. This mother liquor can be recycled upstream, via a mother liquor recycle line (not illustrated), which can for instance be connected to an inlet of the chromatographic separation unit 5 (or to the incoming stream line 5a). This makes it possible to increase the overall yield of the process.

It should be noted that additional treatment units can be provided in addition to, or instead of, some of the treatment units situated upstream and/or downstream of the chromatographic separation unit 5 and described above.

According to the present invention, the raffinate obtained in the step of chromatographic separation is further treated by electrodialysis. Thus, the raffinate line 11 is connected to an inlet of the electrodialysis unit 9.

The raffinate contains impurities separated from the organic acid, but also mineral acid (notably from the eluent). It generally also contains a certain amount of organic acid not properly captured by the bed of stationary phase.

The electrodialysis step produces two streams:
a concentrate (collected in a concentrate line 12 connected at an outlet of the electrodialysis unit 9), wherein charged components are concentrated; and
a diluate (collected in a diluate line 13 connected at an outlet of the electrodialysis unit 9), wherein neutral components are concentrated.

This means that the weight ratio of charged components to neutral components is higher in the concentrate than in the raffinate, and that this ratio is lower in the diluate than in the raffinate.

Charged components include in particular the mineral acid, the organic acid, various cations, and/or salts.

Neutral components include in particular colors and sugars or sugar derivatives (residual carbonizable substances).

Figure 2:
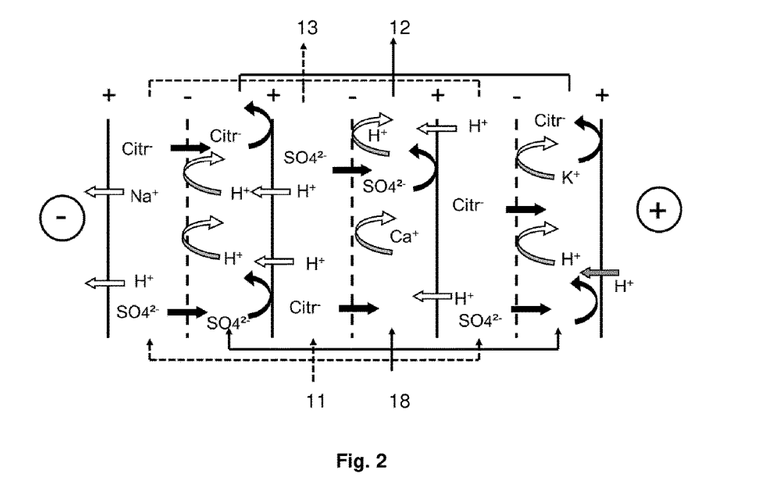
FIG. 2 illustrates one embodiment of an electrodialysis unit used in the present invention, in a schematic manner.

Making reference to FIG. 2, the electrodialysis unit 9 may comprise a stack of anionic and cationic membranes, which are respectively selective to anions and cations. An electric field is applied between a cathode and an anode, so as to achieve migration of the ions through the membranes towards an intermembrane space, where a washing stream from a washing line 18 (also connected at an inlet of the electrodialysis unit 9) is passed. The washing stream may be for instance a water stream. The washing stream as well as the material in the intermembrane space may be recirculated using respective loops. The material in the intermembrane space forms the concentrate and is collected in the concentrate line 12, while the material remaining in solution after ion migration forms the diluate and is collected in the diluate line 13.

The concentration of mineral acid in the raffinate which is subjected to the electrodialysis step can be for instance less than 20 g/L, or less than 10 g/L, or less than 5 g/L, or less than 2 g/L, or less than 1 g/L which is significantly less than typical salt concentrations in streams subjected to electrodialysis in other industrial processes.

The concentrate, containing a major part of the mineral acid, can then be recycled to any step of the process. Therefore, the concentrate line 12 can feed a recycle line which can be connected to any of the units described above. This is meant to also encompass the case where the concentrate line 12 itself is the recycle line.

All of the concentrate can be recycled, or only part of it can be recycled. Furthermore, the concentrate can be divided into two or more parts which are recycled to two or more steps/units (in which case there are two or more recycle lines).

Possible recycling schemes are the following:
the concentrate can be recycled with the incoming stream (i.e. the recycle line is connected to the incoming stream line 5a, or otherwise feeds the chromatographic separation unit 5);
the concentrate can be recycled with the eluent in the step of chromatographic separation (i.e. the recycle line is connected to the eluent line 5b, or otherwise feeds the chromatographic separation unit 5);
the concentrate can be recycled as a feed in the upstream fermentation step (i.e. the recycle line is connected to an inlet of the upstream fermentation unit 1);
the concentrate can be recycled in the upstream filtration step, notably as a diluent, if diafiltration is performed, or as a cleaning stream, for cleaning the filtration membranes before or after the filtration itself is performed (i.e. the recycle line is connected to an inlet of the upstream filtration unit 2);
the concentrate can be recycled in the upstream ion exchange step, notably as a regeneration stream for regenerating the ion exchange resin before or after the ion exchange itself (i.e. the recycle line is connected to an inlet of the upstream ion exchange unit 3);
the concentrate can be recycled in the upstream evaporation step (i.e. the recycle line is connected to an inlet of the upstream evaporation unit 4), notably as a cleaning stream for cleaning the upstream evaporation unit 4;
the concentrate can be recycled in the downstream ion exchange adsorption step or ion exchange step or treatment step on activated carbon (i.e. the recycle line is connected to an inlet of the downstream adsorption unit 6 or similar), notably as a regeneration stream for regenerating the adsorption or ion exchange or other treatment material, before or after the adsorption or ion exchange or other treatment itself;
the concentrate can be recycled in the downstream evaporation step (i.e. the recycle line is connected to an inlet of the downstream evaporation unit 7), notably as a cleaning stream for cleaning the downstream evaporation unit 7;
the concentrate can be recycled in another process, other than the process for producing an organic acid (i.e. the recycle line is connected to another installation.

It should be noted that for each recycling contemplated in the present invention, fresh material, such as fresh water or fresh acidic solution, can be used as well and optionally admixed with the recycled stream.

Making reference again to FIG. 1, optionally, the diluate can be subjected to a concentration step. To this end, the diluate line 13 can be connected to an inlet of a concentration unit 15. This concentration step makes it possible to reduce the volume of effluent which is to be sent to a water treatment plant. The concentration step yields a concentrated fraction on the one hand (recovered in a concentrated fraction line 17), and a diluted fraction on the other hand (recovered in a diluted fraction line 16). Impurities and/or neutral components (colors, sugars or sugar derivative) remaining in the diluate are more concentrated in the concentrated fraction than in the diluted fraction. The concentrated fraction can then be sent to a water treatment plant, while the diluted fraction (or part of the diluted fraction) can be recycled in a similar manner as described above in relation with the concentrate.

The diluted fraction and the concentrate can be recycled to the same step, or they can be recycled to different steps of the process.

The concentration unit 15 can for instance be an evaporation unit or a reverse osmosis unit. Possible evaporation units have already been described above in relation with upstream and downstream treatment of the organic acid-containing stream.

According to a particular embodiment, part of the raffinate can be directly recycled without being processed by electrodialysis. In this case, a direct recycling line branches out from the raffinate line 11 and is connected according to any one of the options described above in relation with the recycling of the concentrate.

It is possible to mix the recycled part of the raffinate with the recycled part of the concentrate and use a single recycle line for both parts.

It is possible to mix the recycled part of the raffinate with the recycled part of the diluted fraction and use a single recycle line for both parts.

It is possible to mix the recycled part of the concentrate with the recycled part of the diluted fraction and use a single recycle line for both parts.

It is possible to mix the recycled part of the concentrate with the recycled part of the diluted fraction and with the recycled part of the raffinate and use a single recycle line for these three parts.

Alternatively, each of these streams can be independently recycled.

EXAMPLES

The following example illustrates the invention without limiting it.

In this example, tests were performed using a citric acid-containing feed obtained from a fermentation broth and filtrated before use. This feed was subjected to a step of chromatographic separation (SSMB), using a 2 g/L sulfuric acid solution as an eluent.

Ten liters of raffinate from the step of chromatographic separation were processed by electrodialysis.

Table 1 below summarizes the characteristics of the raffinate used in the tests.

TABLE 1

| characteristics of the raffinate | |
|---|---|
| Brix | 0.6 |
| pH | 2.11 |
| Conductivity (mS/cm) | 3.65 |
| Color ICUMSA GS 1/3-7 | 9 415 |
| Turbidity ICUMSA GS 2/3-10 | 44 823 |
| Dry solids (%) | 0.54 |
| Ashes (%/dry solids) | 0.078 |

Table 2 below summarizes the characteristics of the electrodialysis equipment used for the trial.

TABLE 2

| characteristics of the electrodialysis equipment | |
|---|---|
| Stack | EDR-Z |
| Anionic membrane | AMH-PES |
| Cationic membrane | CMH-PES |
| Number of cells (pairs) | 10 |
| Surface per cell (m$^2$) | 0.0064 |
| Total active surface (m$^2$) | 0.064 |
| Spacer (mm) | 0.8 |

Table 3 below summarizes the operating conditions for the electrodialysis:

TABLE 3

| operating conditions | |
|---|---|
| Electrolyte | HNO$_3$ at 20 mS/cm |
| Starting material for diluate circuit | 1 L feed |
| Starting material for concentrate circuit | 1 L demineralized water |
| Voltage (V) | 12 |
| Diluate and concentrate flow rate (L/h) | 65 |
| Electrolyte flow rate (L/h) | 45 |

In order to stabilize the membranes, a preliminary run was performed using (instead of the feed) a mixture composed of:

2 g/L of citric acid
0.7 g/L of sulfuric acid; and
0.4 g/L of phosphoric acid.

Thereafter, four consecutive trials using the above feed were performed at a constant voltage of 1.2 V/cell, with intermediate cleaning using water, and with polarity reversal as described in Table 4 below.

TABLE 4

| electrodialysis trials | | |
|---|---|---|
| Trial | Temperature (° C.) | Polarity |
| 1 | 24.6 | + |
| | Water rinsing | |
| 2 | 24.5 | − |
| | Water rinsing | |
| 3 | 24.5 | + |
| | Water rinsing | |
| 4 | 25.7 | − |

In trial 1, samples were frequently collected and analyzed. Trials 2 to 4 were stopped at 0.5 mS/cm conductivity, and the resulting streams were tested for mass balance. The results are shown in FIG. 3, and in Tables 5 and 6 below.

Figure 3:
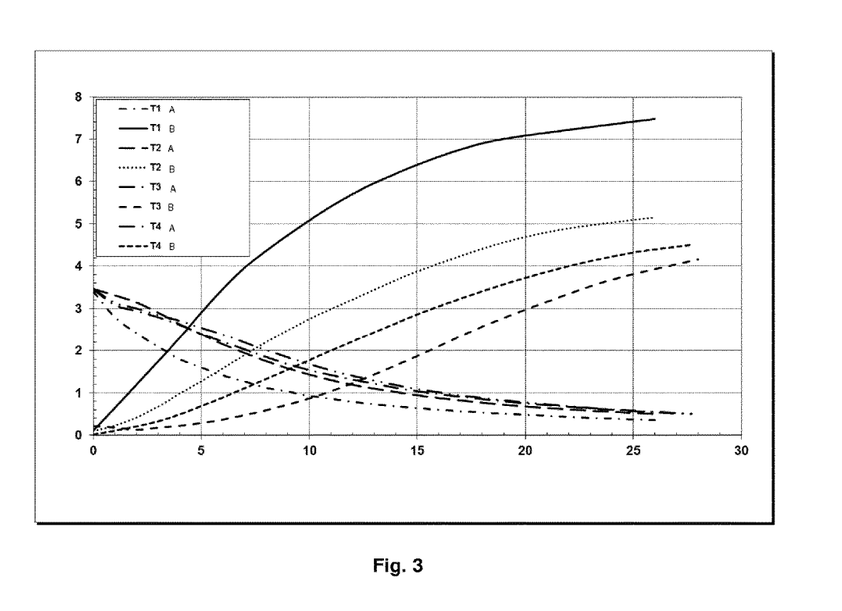
FIG. 3 shows the evolution of conductivity (Y-axis, in mS/cm) over time (X-axis, in min.) for various fractions during an electrodialysis treatment step, as explained in more detail in the example section below.

FIG. 3 shows the evolution of conductivity over time in the diluate (A) and in the concentrate (B), for each of the trials numbered T1 to T4. The increase in conductivity in the concentrate corresponds to an increase in salt concentration in this fraction, while the decrease in conductivity in the diluate shows that salts are progressively eliminated from this fraction.

TABLE 5

| | | results of the electrodialysis trials | | | | | | | |
|---|---|---|---|---|---|---|---|---|---|
| | | Int. (A/m$^2$ mb) | FR (L/h/m$^2$) | pH | Cond. (mS/cm) | Col. | Turb. | DS (%) | Ash (% DS) |
| 1 | D/S | 45.9 | 49.3 | 2.12 | 3.65 | 4656 | 3825 | 0.59 | 8.6 |
| | C/S | | | 3.65 | 0.1 | — | — | 0 | — |
| | D/E | | | 2.97 | 0.37 | 3663 | 7991 | 0.19 | −3.7 |
| | C/E | | | 1.84 | 7.28 | 0 | 0 | 0.30 | 33.0 |
| 2 | D/S | 45.8 | 36.1 | 2.11 | 3.64 | 8481 | 39246 | 0.54 | 10.7 |
| | C/S | | | 3.88 | 0.07 | — | — | — | — |
| | D/E | | | 2.95 | 0.497 | 3330 | 17647 | 0.21 | 3.0 |
| | C/E | | | 1.93 | 5.43 | 500 | 15489 | 0.27 | 29.1 |
| 3 | D/S | 37.6 | 33.5 | 2.11 | 3.76 | 15571 | 88236 | 0.54 | 20.0 |
| | C/S | | | 3.78 | 0.065 | — | — | — | — |
| | D/E | | | 2.91 | 0.525 | 6495 | 21984 | 0.20 | −6.2 |
| | C/E | | | 2 | 4.29 | 666 | 7325 | 0.26 | 26.8 |

TABLE 5-continued results of the electrodialysis trials

| | | Int. (A/ m² mb) | FR (L/h/ m²) | pH | Cond. (mS/ cm) | Col. | Turb. | DS (%) | Ash (% DS) |
|---|---|---|---|---|---|---|---|---|---|
| 4 | D/S | 42.2 | 33.8 | 2.15 | 3.15 | 4192 | 60887 | 0.54 | 17.1 |
|   | C/S |      |      | 3.65 | 0.11 | —    | —     | 0.01 | —    |
|   | D/E |      |      | 2.93 | 0.498| 5496 | 23982 | 0.20 | −0.7 |
|   | C/E |      |      | 1.97 | 4.83 | 1132 | 5527  | 0.26 | 34.8 |

In the above Table, Int. is the average intensity, FR is the average flow rate, Cond. is the conductivity, Col. is the color as determined according to the method cited above, Turb. Is the turbidity as determined according to the method cited above and DS means "dry solids". The abbreviations D/S, C/S, D/E and C/E respectively correspond to the starting material for the diluate circuit (namely demineralized water), the starting material for the concentrate circuit (namely the feed), the diluate collected from the diluate circuit and the concentrate collected from the concentrate circuit when electrodialysis is stopped.

TABLE 6 results of the electrodialysis trials (ionic composition)

| | | $Na^+$ | $K^+$ | $Ca^{2+}$ | Lactate | $Cl^-$ | $SO_4^{2-}$ | $PO_4^{3-}$ | Citrate |
|---|---|---|---|---|---|---|---|---|---|
| 2 | D/S | 40.8 | 12.8 | 63.7 | 111.8 | 21.8 | 569.4 | 418.4 | 1876 |
|   | C/S | 1.0 | 1.8 | 0.7 | 1.0 | 4.4 | 0.79 | 5.9 | 0 |
|   | D/E | 9.8 | 1.4 | 4.3 | 47.5 | 0.0 | 2.6 | 30.5 | 505.0 |
|   | C/E | 130.8 | 9.1 | 1.6 | 24.1 | 107.4 | 682.5 | 271.7 | 1099.0 |
|   | Recovery | 76.3% | 89.1% | 93.3% | 57.9% | 100.0% | 99.6% | 92.8% | 73.4% |
| 3 | D/S | 32.8 | 8.0 | 74.2 | 111.8 | 21.8 | 625.7 | 403.9 | 1536.7 |
|   | C/S | 0.2 | 0.1 | 1.9 | 1.0 | 4.4 | 0.7 | 4.4 | 4.1 |
|   | D/E | 9.3 | 1.2 | 7.9 | 47.5 | 0 | 2.6 | 39.2 | 465.4 |
|   | C/E | 88.3 | 8.2 | 1.7 | 24.1 | 0 | 620.2 | 280.6 | 1183 |
|   | Recovery | 71.5% | 85.0% | 89.3% | 57.1% | 100.0% | 99.6% | 90.2% | 69.4% |
| 4 | D/S | 53.0 | 4.3 | 39.0 | 113.9 | 12.2 | 420.0 | 418.0 | 1837.8 |
|   | C/S | 2.0 | 0.2 | 0.2 | 5.4 | 1.2 | 0 | 19.7 | 9.1 |
|   | D/E | 7.6 | 1.0 | 4.7 | 51.3 | 0 | 1.7 | 31.5 | 403.6 |
|   | C/E | 83.2 | 9.2 | 2.7 | 30.1 | 22.2 | 720.8 | 299.9 | 1058 |
|   | Recovery | 85.6% | 75.6% | 88.1% | 54.9% | 100.0% | 99.6% | 92.5% | 78.0% |

In the above table, all values are provided in mg/mL, except recovery percentages (which provide the weight proportion of each species recovered in the concentrate relative to the feed).

These trials show that at least 99% of sulfuric acid and between 60-80% of citric acid are recovered from the raffinate in the concentrate compartment.

The invention claimed is:

1. A process for producing an organic acid, comprising:
   providing an incoming stream containing an organic acid and impurities;
   subjecting said incoming stream to a step of chromatographic separation, using a solution of mineral acid as an eluent, the eluent containing less than 20 g/L mineral acid, so as to collect an extract and a raffinate, the organic acid being recovered in the extract; and
   subjecting the raffinate to an electrodialysis step, so as to collect a diluate and a concentrate, the mineral acid being concentrated in the concentrate.

2. The process of claim 1, wherein the solution of mineral acid is selected from a solution of sulfuric acid, phosphoric acid, nitric acid, hydrochloric acid and combinations thereof.

3. The process of claim 1, wherein the organic acid comprises citric acid.

4. The process of claim 1, wherein the eluent contains less than 10 g/L mineral acid.

5. The process of claim 1, wherein the diluate is subjected to a concentration step so as to collect a diluted fraction on the one hand and a concentrated fraction on the other hand.

6. The process of claim 1, wherein at least part of the concentrate is recycled with the incoming stream.

7. The process of claim 1, wherein at least part of the concentrate is recycled with the eluent in the step of chromatographic separation.

8. The process of claim 1, wherein providing the incoming stream comprises at least one of the following steps:
   an upstream fermentation step;
   an upstream filtration step;
   an upstream ion exchange step; and
   an upstream evaporation step.

9. The process of claim 1, wherein the extract is subjected to at least one of the following steps:
   a downstream adsorption step, or a downstream ion exchange step, or a downstream treatment step on activated carbon;
   a downstream evaporation step; and
   a downstream crystallization step.

10. The process of claim 5, wherein at least part of the diluted fraction is recycled with the incoming stream.

11. The process of claim 5, wherein at least part of the diluted fraction is recycled with the eluent in the step of chromatographic separation.

* * * * *